United States Patent [19]

Lemelson

[11] Patent Number: 4,665,897
[45] Date of Patent: May 19, 1987

[54] COMPOSITION AND METHOD FOR DETECTING AND TREATING CANCER

[76] Inventor: Jerome H. Lemelson, 85 Rector St., Metuchen, N.J. 08840

[21] Appl. No.: 614,038

[22] Filed: May 25, 1984

[51] Int. Cl.$^4$ ............................................. A61K 49/02
[52] U.S. Cl. ...................................... 128/1.1; 424/1.1; 424/9; 424/450; 264/4.1; 264/4.32; 428/402.2; 128/659
[58] Field of Search ............................... 424/1.1, 9, 22; 264/4.1, 4.32; 428/402.2; 128/1.1, 659

[56] References Cited

U.S. PATENT DOCUMENTS

| | | | |
|---|---|---|---|
| 4,310,505 | 1/1982 | Baldeschwieler et al. | 424/1.1 |
| 4,310,506 | 1/1982 | Baldeschwieler et al. | 424/1.1 |
| 4,311,688 | 1/1982 | Burchiel et al. | 424/1.1 |
| 4,323,546 | 4/1982 | Crockford et al. | 424/1.1 |
| 4,331,647 | 5/1982 | Goldenberg | 424/1.1 |
| 4,334,017 | 6/1982 | Plotkin et al. | 435/7 |
| 4,348,376 | 9/1982 | Goldenberg | 424/1.1 |
| 4,361,544 | 11/1982 | Goldenberg | 424/1.1 |
| 4,429,008 | 1/1984 | Martin et al. | 424/1.1 |
| 4,444,744 | 4/1984 | Goldenberg | 424/1.1 |
| 4,448,765 | 5/1984 | Ash et al. | 424/1.1 |
| 4,460,559 | 7/1984 | Goldenberg | 424/1.1 |
| 4,460,560 | 7/1984 | Tökes et al. | 424/1.1 |
| 4,460,561 | 7/1984 | Goldenberg | 424/1.1 |
| 4,466,951 | 8/1984 | Pittman | 424/1.1 |

OTHER PUBLICATIONS

Grogoriadis et al., Biochem. Biophys. Res. Comm., 65(1975), 537–44.

*Primary Examiner*—Christine M. Nucker

[57] ABSTRACT

Improvements in methods for treating diseases and tumors with compositions of matter defining drug units, each of which includes an antibody, such as a monoclonal antibody produced outside of the body of a living being to be treated. Each unit contains a quantity of normally inactive nuclide capable of being rendered radioactive for treating a disease and a quantity of a second nuclide which may be normally inactive or radioactive, such as a radionuclide. The antibody is targeted to a specific antigen existing in the patient being treated. The drug units emit such radiation upon being activated within the body by radiation such as neutron radiation generated to detect the presence of a particular disease in a living being and to provide an indication of the location and extent of such disease. Once a concentration of disease cells is so located by analyzing signals derived from one or more detectors of radiation generated by a nuclide carried by antibodies to the disease site, and its extent or shape is determined by analysis of direct or reconstructed images of the interior of the body at the site, nuclide material carried to the detected site may be activated by properly controlling the location of a source of activating radiation, its direction and activation to effect treatment of the disease. Treatment radiation may include atomic disintegration of a small quantity of a nuclide, such as boron-10 by absorption of neutrons directed through the body, which disintegration results in the generation of high velocity particles or fragments capable of the localized destruction of diseased cells such as cancer cells.

41 Claims, No Drawings

COMPOSITION AND METHOD FOR DETECTING AND TREATING CANCER

SUMMARY OF THE INVENTION

This invention relates to methods for detecting and treating abnormal tissue growth, such as benign and malignant tumors in living beings including, but not limited to the use of drug units formed of monoclonal antibodies containing or combined with units or small quantities of elements or compounds which either generate low levels of radiation per se or which may be activated to generate radiation for either detection purposes or a combination of detection and treatment purposes. The invention also is defined by new and improved compositions or combinations of matter which may be employed in the carrying out of such methods of detection and treatment.

The instant invention involves improvements in drug units which may be employed for selectively destroying living tissue cells, such as tumor or cancer cells employing small quantities of nuclide elements, such as boron, which may be carried by means of antibodies to specific antigenic sites within a living being afflicted with a disease, such as a malignant or benign tumor or a number of such tumors or malignancies. Improved methods for utilizing such prior and novel compositions to optimize or improve treatment of the malady are also presented herein and define part of the instant invention.

It is known in the art to produce and employ antibodies, such as monoclonal antibodies, and to tag same with a radioactive material for the detection of their location within a human being. It has also become known to employ a normally inactive nuclide, such as boron, tagged to an antibody to deliver it to a particular antigen within a human body such as cancer cells.

I have conceived to employ such a nuclide as boron either during its activation within the human body by externally applied radiation and its employment to destroy malignant cells or without such accompanying cell destruction, for detecting the presence of concentrations of antigenic material and the location of such material within a living being.

The instant invention employs specially prepared combinations of either a small quantity of a single nuclide or respective small quantities of a plurality of nuclides with respective antibodies, such as monoclonal antibodies, targeted to a specific antigen or antigens existing within a living body. When caused to enter the bloodstream of a living being, such combination or combinations of antibody and nuclide will concentrate at one or more sites within the living being when the antibodies target the drug unit to antigenic matter, such as malignant cells, at such site. Thereafter, one or more of a number of procedures may be employed to utilize the drug in either detecting the presence of the antigenic cells at such site or sites, the density thereof of shape of the growth containing such antigenic cells and the location of the growth or cell concentration within the body to permit proper diagnosis and treatment to be effected.

In an important form of the invention, the scanning and detection is effected of a drug which is targeted to a specific antigen, by radiation which is given off by the drug as a result of activating units of a normally inactive nuclide, when so located, by means of externally generated activating radiation such as one or a plurality of beams of neutrons. The radiation given off by the activated units of nuclide material may be of a low, but detectable, radiation level wherein only the local cells are subjected to such low level radiation. In another form, the radiation which is employed for detection or monitoring purposes is also employed for treatment purposes and monitoring, together with treatment initiation occur substantially simultaneously. The nuclide units employed in combination with respective single antibodies may thus be single nuclides, such as boron 10, which are capable of atomically disintegrating and emitting cell killing radiation or particles, a combination of a radionuclide and a normally inactive nuclide which is capable of being activated by externally generated radiation, such as neutrons, passed through the body of the patient after one or more concentrations of the drug units have been detected by the radiation emitted by the radionuclide material comprising part of the drug units. In a third form of the invention, two normally inactive nuclide materials are combined to form a common drug unit together with an antibody, one of which is activatable by external radiation but produces low level detectable radiation when so activated while the other is activated by externally generated radiation and, when so activated, produces radiation effects, such as miniature atomic explosions, which are employed to destroy diseased or cancerous tissue. In yet another form, a single nuclide material may be activated by external radiation, such as a beam of neutrons, to generate a low level of detectable radiation when activated by low intensity external radiation or a higher level of cell killing radiation when activated by a higher intensity of external radiation.

Accordingly it is a primary object of this invention to provide new and improved combinations or compositions of matter which are useful in detecting concentrations of antigenic material, such as tumors and the like, located within living beings.

Another object is to provide new and improved compositions or combinations of matter useful in both detecting and treating or destroying certain types of diseased tissue, such as malignancies, tumors and the like.

Another object is to provide a new composition of matter which includes at least two different nuclide materials, one of which may be used for generating low level detectable radiation for monitoring and diagnosing concentrations of antigenic material in a living being while the other may be used to treat or destroy such antigenic material, such as cancerous cells, existing or growing within the living being.

Another object is to provide new compositions of matter useful in the treatment of tumors and malignancies which include units defined by at least one antibody, such as a monoclonal antibody, at least one small quantity of a normally radioactive nuclide, such as radioactive iodine and at least one small quantity of a normally inactive nuclide capable of being rendered radioactive when subject to radiation such as neutron radiation.

Another object is to provide a new composition of matter formed of separate units which include respective antibodies and respective small quantities of two nuclides, both of which are normally inactive and are respectively capable of being rendered radioactive when subject to different intensities of externally generated radiation.

Another object is to provide a new composition of matter formed of separate units which include respective antibodies and respective small quantities of two nuclides, both of which are normally inactive and are respectively capable of being rendered radioactive when subject to different quantities of externally generated radiation.

Another object is to provide a new composition of matter formed of separate units which include respective antibodies and respective small quantities of two nuclides, both of which are normally inactive and are respectively capable of being rendered radioactive when subject to different types of externally generated radiation.

Another object is to provide new and improved methods for employing and utilizing the new drug units disclosed herein for treating one or more disease conditions existing in a living being, such as a malignancy and other forms of cancerous growth.

Another object is to provide a new and improved method for sequentially detecting and treating or destroying diseased tissue existing within a living being.

Another object is to provide a method for simultaneously monitoring diseased tissue, such as one or more tumors, and treating or destroying a portion or all of such diseased tissue by means of a single drug.

Another object is to provide a method for both detecting and destroying tumors and the like utilizing a drug which is targeted to the tumor and which has the ability to be activated at the site of the tumor and generate both detectable and treatment radiation, when triggered from the exterior of the body of the person being treated.

Another object is to provide a method of treating a tumor with radiation which is generated at the site of the tumor and is so limited in intensity or effect that little, if any, normal tissue cells are detrimentally affected or destroyed during the employment of such method.

Another object is to provide a method of treating a tumor by incrementally destroying the cells of the tumor with radiation generated intermittently at the tumor site.

Another object is to provide a method of treating and destroying a tumor or malignancy by the repeated application of radiation generated at the site of the malignancy in such a manner as to optimize the treatment and minimize the destruction or deterioration of normal cells.

Another object is to provide a method of treating a malignancy existing within a living being by utilizing drug units which may be rendered radioactive at the site of the malignancy so as to minimize the effects of radiation on normal tissue during the delivery of the drug units to such site wherein computerized monitoring is employed to control the treatment in response to signals generated by detecting radiation emitted from the site of the malignancy.

Another object is to provide new and improved combinations or compositions of matter which are useful in effecting computer control of treatment of human maladies employing such drug units.

With the above and such other objects in view as may hereinafter more fully appear, the invention consists of the novel compositions of matter and methods of producing and utilizing same to detect the existence of certain diseases, such as cancer, and the treatment of such diseases in a living being as more fully described herein, but it is to be understood that changes, variations and modifications may be resorted to which fall within the scope of the invention as claimed without departing from the nature and spirit of the invention.

DETAILED DESCRIPTION

In a first and preferred embodiment, a small quantity of a nuclide such as boron-10, varying from an atom or a number of atoms thereof, is combined with an antibody, such as a monoclonal antibody and a second nuclide, such as one of the radionuclides or normally inactive nuclides hereafter described to form a drug unit, a multitude of which units are employed as a treatment dose, preferably mixed in a quantity of water. The monoclonal antibody has a particular specifity or antigenic determinent characteristic such that it will seek and attach itself and the drug unit is it part of to a specific antigen, such as a cancer cell, virus or bacterium existing in a living being. Boron-10 will undergo the following reaction when activated by neutrons:

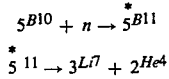

In the above reaction, an atom of boron-10 absorbs a neutron forming the radiactive isotope boron-11 which disintegrates into Helium-4 and Lithium-7 as fragments with high kinetic energy capable of destroying thousands of cells of adjacent tissue, such as cancer cells which are in the trajectories of such fragments. Since the penetration of such fragments is in the range of a milimeter or less, the reaction is only locally destructive to cells and may be concentrated at a tumor site under proper control to destroy primarily the diseased or cancerous cells to which the drug units are targeted by the antibodies thereof.

The following examples define methods for producing drug units or components of drug units which include antibodies and one or more nuclides for treatments and use as described herein:

EXAMPLE 1

A quantity of antibodies, such as monoclonal antibodies which are targeted to a specific antigen or group of antigens, are suspended in water to which an acqueous solution of boric acid in a molar ratio of antibody/acid of about 1/1 to 1/6 has been added and the mixture is subjected to agitation for a period of 24 hours. The antibody is then precipitated with ethanol, acetone or tetrahyrrofuran, filtered and freeze dried. The boron containing antibody may be used per se as described hereafter treated or combined with a second nuclide, such as described hereafter, in a similar manner or the second nuclide may be added to the original boric acid solution to combine it with the antibody at the same time the boron is combined therewith. The antibody-nuclide(s) units may be stored per se or incorporated into water or other liquid which is frozen for future application to a living being as described.

EXAMPLE 2

The procedure of Example 1 is carried out at pH3 obtained by adding a suitable amount of acetic acid to achieve the pH state.

EXAMPLE 3

The procedure of Example 1 is carried out to provide a hydrogen ion concentration which is slightly basic, approximately pH8 by adding a proper amount of sodium bicarbonate or the like to the aqueous solution containing the reagents of Example 1.

EXAMPLE 4

A dimethyl sulfoxide solution containing the desired antibody is agitated by suitable means to bring the components into intimate contact and is treated with a molar ratio of 1 to 1 of boron oxide powder dissolved in such solvent. The mixture is used per se or is combined with a second nuclide in powder form, such as one of the radioactive nuclides or normally inactive nuclides capable of being rendered radioactive with neutrons or other radiation defined hereafter, and is agitated for 24 hours. Ethyl ether is added to the DMSO solution until the nuclide tagged antibodies precitate therefrom. The precipitate is separated from the liquor, washed with ether and dried for storage or stored per se.

EXAMPLE 5

Suitable antibodies and sodium cyanoborohydride are placed in a container of tetrahydrofuran in a molar ratio of 1 to 2 and the mixture is agitated for 18 hours resulting in the $BH_3$ moity attachment to the antibodies. Treatment of the product with hexane precipitates the antibodies containing boron-10. The latter is filtered and washed with 80% ethanol until free of sodium cyanide. The product may be further treated to combine it with a second nuclide as described hereafter such as cadmium 113, gadolinium 157, samarium-149, mercury-199, lithium-6, etc. or a radionuclide which generates detectable radiation, as described hereafter. The antibodies are dried and stored at zero degrees Centigrade.

Boron of the type described, or otherwise composed, may also be incorporated into antibodies using derivatizing agents that already contain boron in the form of boronic acid or its esters and further containing a derivatizing group Y. The general formula for suitable derivatizing agents is:

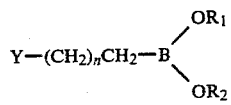

FIG. 1 where $R_1$ and $R_2$ can be either an alkyl group such as ethyl, propyl, butyl, etc., hydrogen or an aryl group such as phenyl; or substituted phenyl groups. Group Y is a derivatizing group such as described herein and n can be 0, 1, 2, 3 or up to 20.

Amoung the derivatizing groups Y which may be employed, are, for example, a halogen such as fluorine, chlorine, bromine or iodine; an acyl halide group

where X is fluorine, chlorine, bromine or iodine, a carboxylic acid, a hydride group such as $$(-\overset{O}{\underset{\|}{C}}-O-\overset{O}{\underset{\|}{C}}-R),$$

where R is hydrogen, alkyl or aryl; an azide group ($-N_3$), an epoxide group $$(\overset{\diagup C_o - C \diagdown \overset{R_2}{\diagup}}{\underset{R_1}{}\phantom{xx}\underset{R_3}{}})$$

where $R_1$, $R_2$, $R_3$ may be hydrogen or an alkyl moiety, a diazonium group group ($-N_2\oplus$); an isocyanate group ($-NCO$), an isothiocyanate group ($-NCS$); a hydrazide group ($-NH-NH_2$); an azomethane group $$(\overset{R}{\diagdown}{CN_2})$$

where R may be hydrogen, alkyl or an aryl radical; an alpha-haloester group $$(\overset{O}{\underset{\|}{C}}-\overset{}{\underset{X}{\overset{\|}{C}}}-O-R)$$

where X is fluorine, chlorine, bromine or iodine and where R is hydrogen or an alkyl group and R' is an alkyl group such as methyl or ethyl. Carbonyl groups $$\overset{O}{\underset{\|}{-C-}}$$

such as present in aldehydes and keytones are suitable derivatizing radicals and the carbonyl group present as

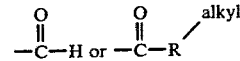

is suitable as a reactive terminal in FIG. 1.

Table 1 illustrates examples of chemical links formed by selected derivatizing agents Z—Y-links which attach the boron containing moiety Z to the molecules of antibodies ANB or monoclonal antibodies MAb. Such methods of attachment are known in the art.

TABLE 1

| Attachment of the Functional Group Y of the Derivatizing Agent Z—Y to the Functional Groups of Antibodies ANB—Q. | | | | | |
|---|---|---|---|---|---|
| Antibody ANB—Q | | Derivatizing Agent Z—Y | | Attaching Link Between ANB and Z | |
| Generic Name of Q | Formula | Generic Name of Y | Formula | Link Name | Formula |
| hydroxyl | ANB—OH | acyl halide | $Z-\overset{O}{\underset{\|}{C}}-X$ | ester | $Z-\overset{O}{\underset{\|}{C}}-O-ANB$ |
| " | " | anhydride | $Z-\overset{O}{\underset{\|}{C}}-O-\overset{O}{\underset{\|}{C}}-Z$ | " | " |

TABLE 1-continued

Attachment of the Functional Group Y of the Derivatizing Agent Z—Y to the Functional Groups of Antibodies ANB—Q.

| Antibody ANB—Q | | Derivatizing Agent Z—Y | | Attaching Link Between ANB and Z | |
|---|---|---|---|---|---|
| Generic Name of Q | Formula | Generic Name of Y | Formula | Link Name | Formula |
| " | " | isocyanate | Z—NCO | urethane | Z—N(H)—C(=O)—O—ANB |
| amino | ANB—NH$_2$ | acyl halide | Z—C(=O)—X | amide | Z—C(=O)—N(H)—ANB |
| " | " | anhydride | Z—C(=O)—O—C(=O)—Z | " | " |
| " | " | isocyanate | Z—NCO | urea | Z—N(H)—C(=O)—N(H)—ANB |

Q is the functional group of the antibody ANB—Q.
Y is the functional group of the derivatizing agent Z—Y.
Z is the boron containing moiety of the molecule of the derivating agent Z—Y.
ANB is the molecule of the antibody minus the functional group Q.
X is a halogen atom such as fluorine, chlorine, bromine, or iodine.
Z may also be any other suitable nuclide containing moiety.

The examples cited may thus generally be used for incorporating boron into proteins by attachment of the boron containing moiety to unshared electronc pair orbitals on such elements as nitrogen, oxygen and sulfur.

The amino groups, amide groups, imide groups, guanidino groups, aminide groups, hydrozyl groups and sulfy dryl groups present in the protein structures may be used as terminals for the incorporation of the boron into the antibodies or monoclonal antibodies. Among the derivatizing agents thus employable are boric acid and its esters, boron oxide, butaneboric acid and its esters, phenylboric acid and its esters, tetrafluoroboric acid, diborance, boron halides, boron trifluoride, boron trichloride and boron tribromide, borane complexes of amines such as borane diethylaniline complex, borane trimethylamine complex, borane butylamine complex, borance-morpholine, borane-pyridine complex, borane-2, 6-lutidine complex, borane-tetrahydrofuran complex, borane-triethylamine complex, borane methyl sulfide complex, catechol borane, sodium cyanoborohydride, boron trifluoride methanol complex, complexed of boron trifluoride with amines, tetrahenylboron sodium, triethanolamine borate, sodium borohydride. perhydro-9b-boraphenalene and the special function agents set forth herein.

Due to the fact that the molecular weight of the antibodies or monoclonal antibodies employed is in the range of millions and the molecular weight of the boron containing moieties is in the range of thirteen to hundreds, and the molar ratio of the antibody relative to the boron containing moiety is kept relatively high in the reactions described, the boron containing moiety attaches itself statistically to both the active and inactive segments of the antibody relative to the antigen and at least a part of the antibody remains active relative to the antigen to which it targets. Similarly, moieties which contain a second nuclide, such admium-113, lithium-6, samarium-149 or any of those described herein including a radionuclide, may be employed to attach such plurality of nuclides to the antibodies thus providing drug units which may be employed to detect concentrations of the drug units before effecting activation of the cell killing radiation as described.

In employing antibodies, such as monoclonal antibodies targeted to a specific antigen, for disposing a nuclide such as boron-10 immediately adjacent or within a malignancy within the body of a living being, suitable detection of the site or sites at which the antibodies are located after they have targeted or attached themselves to the antigens or malignancy or tumor(s) at such site, must be effected to permit the beam or beams of externally generated neutrons to be properly directed through the body of the patient. Such monitoring may be effected by the detection of radiation emitted from the antibodies at the tumor site(s). The monoclonal antibodies described, which have been combined with one of the described nuclides, such as boron-10, may also be combined with such radionuclides as cobalt-57, galium-67, cesium-131, iodine-131, iodine-125, thalium-201, technecium-99m, indium-111, selenium-75, carbon-11 or nitrogen-13 or combinations of such radionuclides. The latter two nuclides emit positrons and produce gamma rays which are formed by the positron-electron pair anihilation. In a preferred form, one of the radionuclides iodine-125, iodine-131, nitrogen-13 or carbon-11 are introduced either directly into the antibody or the derivatizing group, such as presented above. Iodine, for example, may be directly combined or introduced into the antibody or the derivatizing group of FIG. 1 by utilizing sodium iodide and Chloramine-T or by utilizing sodium iodide and hydrogen peroxide in the presence of the enzyme lactoperoxidase which is immobilized on an ion exchange resin. Nitrogen-13 and carbon-11 may be so introduced by standard synthetic reaction methods which are well known in the art. Electrolytic iodination with sodium iodide may also be effected to accomplish the desired results of combining the iodine radionuclides with the antibodies or derivatizing group.

In another form of the invention, stable nuclides may also be combined with or introduced into the antibodies or derivatizing agent of the type mentioned above to be selectively activated when targeted by the antibodies adjacent and close to an antigen, such as diseased or malignant tissue or cells by directing activating radiation such as a beam of neutrons at the targeted nuclide wherein the resultant radiation emitted by the nuclide particles or atoms of the combined antibody-nuclide units may be employed to detect and locate the antigenic material in the living being to which the medication units have been administered and, if desired, to provide emitting radiation which may highlight and define visual information such as a direct or computer generated image of a malignancy or non-malignant tumor or other malady or abnormality existing within the living being. Such stable nuclides, which have high enough thermal neutron cross sections which may be caused to become radioactive for generating detectable radiation for detection and imaging purposes, include the following: (a) Cadmium-113 with a thermal neutron cross-section of 20,000 barns; boron-10 (3400 barns); gadolinium-157 (240,000 barnes); gadolinium-155 (58,000 barns); samarium-149 (41,500 barnes); mercury-199 (2000 barns); lithium-6 (960 barnes). The immediately generated gamma rays resulting from a pulse of neutrons directed through the body along a path to intersect the nuclide units at the site of the body or tumor being treated may be detected and measured or employed to generate a direct and/or computer graphics generated image by suitable sensing means and/or the secondary gamma rays may be so detected and utilized as described.

In a particular form of the invention, a stable nuclide such as boron-10 may be employed, as described, to perform both the functions of detecting and/or imaging an antigentic area or malignancy of a living body and the function of destroying local tissue as described by means of the high velocity, high energy gamma rays and lithium-7 fragments which are produced when the boron-10 absorbs one or more neutrons and converts to the excited state of boron-11. In yet another form, a second particle or atom of a second nuclide, such as one of the types described above, may be incorporated with the monoclonal antibody, as described, and may be utilized for tumor localization by gamma ray emission and for gamma ray scintillation monitoring purposes. Such second nuclide may also be operable, when so activated with neutrons, to generate high velocity fragmentary material or particles which may cooperate with the particles of the first nuclide in destroying malignant tissue, non-malignant tumors, bacteria or other antigenic matter existing within a living being and requiring such destruction for proper health and normal functioning. For example, separate units of a nuclide, such as boron-10 or the like may be disposed within or adjacent to an obstruction, such as a blood clot, plaque matter or other form of living or non-living matter which is obstructing or restricting the flow of a body fluid such as blood or other fluid and activated thereafter by suitably generated and directed radiation, such as a beam or beams of neutrons generated externally of the living being under treatment and directed through the body. The resulting localized miniature atomic explosions of each of the units or particles of nuclide may be employed to destroy the cells or living and/or dead tissue or other matter forming the blockage or restriction in a manner whereby it may be removed or will flow from the side of the blockage or restriction and be excreted or otherwise expelled from the body without the need for surgery or invasion of the body with a tool or with minimum use of invasive tooling and surgery. A select amount of the nuclide in solution or liquid carrier may be administered to the blockage material by injection needle and/or, as described, by targeting units containing the nuclide with antibodies attached thereto.

In utilizing the drug or medication units described herein for the treatment of both malignant and non-malignant tumors by targeting nuclides to the sites thereof with antibodies such as monoclonal antibodies produced to target to specific antigens such as the cells of the tumor and/or an organ in which the tumor exists, or in the treatment of other maladies, such as a disease characterized by a localized infection or a blockage of a passageway which may be alleviated or abated by the localized application of explosive and/or non-explosive atomic radiation, the tumor or infectious site to be so treated is first detected. Such detection may be effected by such techniques as photographs and/or electronic imaging using X-rays, ultrasonic radiation, so-called nuclear magnetic resonance (NMR) andd, in certain instances, employing computer axial tomography (CAT) scanning with computer generated imaging of the afflicted site.

After the site of the tumor or other malady is determined, a first quantity of one of the described drug or medication units containing one or more nuclides and antibodies as described, is administered to the person or animal being treated by injection or injestion and such units are allowed to target to the tumor or disease site. The next step may involve either activating the detection radiation generating nuclide to indicate that the existance of the nuclide material at such site and/or image same or to initiate treatment without such indication. If the detection nuclide is initially radioactive, as described, such radioactivity may be detected to outline or otherwise indicate the shape and extent of the malignancy or malady. Other suitable activating radiation may be employed to activate the nuclide. Thereafter, radiation such as a beam of neutrons may be properly directed to intersect the site or organ containing the antibody units, activate the nuclide units thereat and effect local nuclear reactions as described for destroying cancerous or non-malignant tissue cells immediately adjacent the nuclide units.

If a gamma radiation generating nuclide, which is either radioactive per se or may be rendered radioactive when suitable radiation such as neutron radiation is directed thereat, is incorporated into the drug units described, and such units are injected or otherwise administered to a living being having a malignant or non-malignant tumor or group of such tumors, an abnormal growth or obstruction or other malady to be treated with radiation, and such units are permitted to target to the antigens to which the antibodies of the units are targetable at the site of the tumor, scanning of the gamma radiation generated at such site by suitable detection means may be employed to determine such variables as tumor localization and location, the extent of filtration and distribution of the antibody containing drug units into the tumor or antigenic matter (through capillaries and lymphatic passageways), the distribution of the drug units without the tumor, tumors of antigenic matter, the shape and size of the tumor(s) or tumor mass and the location thereof, the presence or absence of metastases in other areas or locations of the body and the extent, size and shape thereof. In certain instances, it may be desireable or necessary to combine drug units as described containing antibodies, either as part of each unit or separate units, which are targetable to different antigens such as different types of cancer cells, organs or other antigenic matter which may exist within a living being, to permit the simultaneous or sequential monitoring by gamma radiation detection so as to effect the detection and determination of the location(s) and extent of other maladies, such as other diseases or cancers existing within the body of the patient being treated or diagnosed.

Such monitoring and detection may be carried on during and/or after effecting the described neutron radiation of the site containing the tumor, abnormal growth or blockage to be radiation treated or removed, so as to derive information relating to both the extent and location of the growth and its diminuation or destruction resulting from the nuclear and chemical processes which occur as a result of the radioactivity of the nuclide units activated at the site of the growth. The effects, if any, of such controlled radioactivity on adjacent normal tissue may also be monitored by means of such radiation and/or auxiliary radiations generated externally of the body.

The procedure(s) described above may be repeated a number of times with respect to the application of a single dose of such drug units to a patient as portions of such single dose become targeted to respective portions of the antigenic material being treated and/or with respect to additional doses of such drug units administered after the initial dose or the portion thereof which has targeted to a specific site has been rendered radioactive. By such repeated treatment with controlled radiation, cells of a tumor or abnormal growth may be incrementally destroyed until the entire tumor is destroyed or so weakened that the normal immune system of the body may destroy the remaining portion of the tumor or tumors at the site under treatment.

In yet another form of the invention, a single nuclide may be utilized to both detect and monitor one or more of the variables described above and to effect radiation treatment of the abnormal growth or blockage as described. Such monitoring may be effected by detection of the radiation emitted during the treatment phase of the medical procedure such as, for example, when boron-10 is converted to boron-11 by neutron bombardment or when the nuclide is subjected to external radiation sufficient to cause it to become radioactive without atomically disintegrating to form the described high velocity cell destroying particles.

It is noted that while the preferred embodiments of the invention involve the provision of units of a drug which include a single antibody, such as a monoclonal antibody targeted to a specific antigen which may exist in the living being being diagnosed and/or treated and a single nuclide unit for treatment, with or without the inclusion of a second nuclide unit in the drug unit or in other drug units combined therewith for detection and monitoring purposes, such drug units may be varied in structure as described and may contain additional units of the same or different nuclides and two or more of the same or different antibodies attached thereto for targeting to different antigenic materials or cells.

The nuclides described may also be encapsulated within organic or inorganic polymers or protein masses, or microcapsules of same which form part of each individual unit of such drug or medication. The encapsulant or microcapsule may also be biodegradable to facilitate its elimination from the body or may be eliminated as a unit by normal process if not destroyed during the described treatment by the radiation generated.

In utilizing the described new composition of matter or drug units to treat a disease such as cancer in the form of a malignancy or tumor, one or more of a number of procedures may be carried out to effect proper treatment, viz:

1. In a first procedure, one or more known methods may be employed to detect the presence of cancer in a living being and the general location of such cancer, such as by chemical analysis of body fluid(s), direct X-ray scanning and imaging, computerized axial tomography (CAT) scanning using X-rays, nuclear magnetic resonance or the like, ultrasonic scanning, etc. One or more of the described drug units may then be prepared or derived from a drug unit bank produced from monoclonal antibodies which are targeted to the particular type of cancer discovered. They may then be administered by injection and/or oral means to the person undergoing diagnosis and treatment, wherein either the radionuclide is employed to precisely locate and outline or image the tumor or tumors and/or nuclide material delivered to the site by the units rendered radioactive as described at the site to generate radiation of such a configuration as to provide the detection means with signals capable of being processed and analyzed by direct and/or CAT scanning means to permit the construction of computerized images of the site and the tumor thereat and/or direct images of the radiation emitted. After the information is so obtained and analyzed either by an expert, such as a radiologist, and/or by computer analysis, a source of nuclide activating radiation capable of rendering the nuclide capable of generating cell killing or modifying radiation is properly directed at the body of the living being such that it intersects the drug units and the nuclide material thereof at the site of the tumor or malignancy and renders same explosively radioactive in a manner to effect the destruction of the tumor or a substantial number of cells thereof to either facilitate additional similar treatment or permit the immune system of the body to destroy the tumor.

2. In a second method, the radioactivity generated by the described radionuclide provided in all or certain of the drug units which become targeted to the antigens of the tumor(s) at the site of the disease, generate sufficient radiation when so concentrated to be detectable and to permit one or more detectors such as scintillation counters and/or television cameras which are properly supported outside of the body, to generate output signals which contain information about the tissue at the site of the disease or tumor which information may be computer analyzed and/or used directly in the generation of an image or images of the site, either by directly exposing film and/or by computerized image analysis and reconstruction. Thereafter treatment as described with radiation generated by activating the nuclide which generates cell killing or modifying radiation is caused to proceed with the activating radiation properly directed and controlled by computer or other means in accordance with the location and extent of the tumor(s) so detected and located.

3. In a third method which may be combined with either or both the two methods described above, part of the radiation generated when the nuclide units at the site are caused to atomically react or explode, is detected by suitable detection means such as one or more scintillation detectors and/or other detection transducing means such as a television camera or cameras properly modified to effect image generation on a video display screen, to provide an image indicative of either the location and extent of the nuclear reaction and/or the results of such reaction involving those units of nuclide material existing in the drug units which have been rendered radioactive with such externally generated radiation such as neutrons directed as a beam or beams at the site.

In another form of the invention, drug units as described containing a plurality of different monoclonal antibodies which are targeted to different antigens may form the dose thereof which is administered to the patient being diagnosed and treated and may contain either the explosive radionuclide and a radioactive nuclide or a nuclide capable of generating detectable radiation per se as described. A dose of such units may be administered to a living being hava plurality of different maladies, such as different cancers and may be employed to treat or destroy same either simultaneously or sequentially with externally applied radiation such as one or more beams of neutrons properly directed at the site or sites of such tumors.

While the five examples hereinbefore described for incorporating a nuclide into an antibody or forming a drug unit of a nuclide and specific antibody involve the nuclide boron which is activatable or made radioactive in an explosive manner by directing neutrons as a beam at concentrations of the drug units targeted to cites containing the antigens to which the antibodies of the units are targeted, other nuclides may also be employed tagged or combined with such antibodies, which may be selectively applied and activated under monitored control to optimize treatment of a variety of diseases or maladies, such as cancerous tissue and tumors and various forms of other diseases involving bacteria, virus and malformed or malfunctioning body tissue. In addition to boron, isotopes of hydrogen, lithium, berylium, cadmium, lanthanum and other heavy metals may be employed as may the actinide series of elements and so called transition elements.

By selecting one of the nuclides available to become radioactive with activating radiation, such as neutron radiation or other forms of activating radiation, radioactivity in different forms may be employed to treat the specific malady detected and may include emission of alpha and/or beta particles, protons, positrons, gamma rays, antiprotons and the like. In addition, such site activated radiation may include nuclear fizzion and neutron manipulation. By selectively choosing the type of emission or radiation desired or a plurality of such types as a result of the selective choice of nuclide or nuclides to form the drug units, the drug units may be employed as described to destroy cells, such as cancer cells of a tumor or malignancy for distances which are less than one tenth of an inch from the activated nuclide or greater depending on the concentration and distribution of the nuclide or nuclides at the site, the nuclide or nuclides employed and the concentration and duration of the activating radiation employed in the medical procedure or treatment described.

I claim:

1. A composition of matter comprising in combination
   (a) a multitude of drug units, each unit defined by a antibody targeted to a specific antigen in a living being, and a first quantity of a first normally inactive nuclide integrally secured to said antibody,
   (b) said first quantity of said first nuclide being capable of being rendered radioactive when suitable radiation generated externally of said drug unit is directed at said nuclide, and
   (c) a quantity of a second, normally inactive nuclide integrally secured to said drug unit,
   (d) said second nuclide being renderable radioactive when it is subjected to externally generated radiation, wherein the degree of such radioactivity of the activated second nuclide may be electronically detected and, upon being so detected may be employed to trace and locate a multitude of said drug units within a living being,
   (e) said first nuclide being operable to generate, when activated with externally generated radiation, radioactive radiation of an intensity which is substantially greater than the intensity of radioactive radiation generated by said second nuclide and wherein said radioactive radiation generated by said first nuclide is of such a characteristic as to permit it to destroy living tissue cells in the vicinity of said drug unit.

2. A composition of matter in accordance with claim 1 wherein said first and second nuclides are selected from nuclide elements including those of boron, cadmium, hydrogen, samarium, lithium, gadolinium and the like.

3. A composition of matter in accordance with claim 3 wherein said first and second nuclides are selected from the same group of nuclides but exist in different quantities in said drug unit.

4. A composition of matter in accordance with claim 3 wherein said first nuclide is greater in quantity than said second nuclide in said drug unit.

5. A composition of matter in accordance with claim 1 wherein a liposome contains said first and second nuclides and supports said biological element which defines at least a portion of the surface of said drug unit.

6. A composition of matter in accordance with claim 1 including a solid substrate defined by a miniature fat globule containing said quantities of said first and second nuclides and supporting said antibody.

7. A composition of matter in accordance with claim 1 wherein said substrate is a polymer.

8. A composition of matter in accordance with claim 7 wherein said substrate is a synthetic resin.

9. A composition of matter in accordance with claim 7 wherein said substrate is an organic polymer.

10. A composition of matter in accordance with claim 1 wherein each of said drug units includes a substrate comprising a quantity of solid protein supporting said quantities of said first and second nuclides.

11. A composition of matter in accordance with claim 1 wherein each of said drug units includes a substrate formed of a fat.

12. A composition of matter in accordance with claim 11 wherein
    said substrate is a liposome, and
    at least one of said nuclides being disposed within said liposome.

13. A composition of matter in accordance with claim 1 wherein said antibody and said first and second nuclides are incorporated into said antibody by a derivatizing agent which is selected from the group of polymers which include esters, urethanes, amides and ureas.

14. A composition of matter in accordance with claim 1 wherein said antibody and said nuclides are secured together by a derivatizing agent which is selected from the group of polymers including hydroxyl halides, anhydrides, isocyanates and amion acyl halides, anhydrides and isocyanates.

15. A composition of matter in accordance with claim 1 wherein said antibody is a monoclonal antibody targeted to a specific antigenic material defining a specific diseased cell.

16. A composition of matter in accordance with claim 22 wherein said biological element is a monoclonal antibody targeted to a specific antigenic material defining a specific cancer cell.

17. A composition of matter in accordance with claim 1 wherein
said antibody, said first nuclide and said second nuclide form a drug unit which is targeted to a specific antigen in a living body,
further comprising a carrying liquid containing a multitude of said drug units and forming a drug dose to be administered for treatment to the body of a living being.

18. A composition of matter in accordance with claim 17 wherein said multitude of said drug units are supported in a liquid for injection administration thereof to the bloodstream of a living being.

19. The composition of matter in accordance with claim 1 including a plurality of antibodies secured to said drug unit.

20. A composition of matter in accordance with claim 1 wherein said first nuclide is a single atom capable of being exploded when subjected to neutron bombardment from an external source of neutrons.

21. A composition of matter comprising:
(a) a drug unit containing an antibody targeted to a specific antigen existing in a living being, and a first quantity of a first normally non-radioactive nuclide combined with said antibody,
(b) said first nuclide capable of being rendered radioactive with radiation generated externally of said drug unit and directed at said first nuclide,
(c) said first nuclide being combined with a quantity of a second nuclide which is normally non-radioactive disposed in said drug unit with said first nuclide,
(d) said second nuclide capable of being rendered radioactive with radiation generated externally of said drug unit and directed at said second nuclide,
(e) said first nuclide capable of generating cell destroying radioactive radiation when activated with external radiation,
(f) said second nuclide capable of generating radioactive radiation of a lower intensity then the radioactive radiation generated by said first nuclide when activated with eternally generated radiation, wherein said lower intensity radioactive radiation is capable of being detected by suitable detection means disposed outside of a living body containing said drug unit to permit the movement and location of said drug unit to be monitored and tracked from outside the body containing said drug unit.

22. A composition of matter in accordance with claim 21 wherein
there is a plurality of said drug units, and
said second nuclide is selected from the group of nuclides which includes boron-10, cadmium-113, lithium-6, samarium-149, mercury-199, gadolinium-155 and gadolinium-157.

23. A composition of matter in accordance with claim 22 wherein
said second nuclide is capable of being rendered radioactive when subjected to neutron bombardment, and
said second nuclide being substantially less in quantity than said first nuclide in said drug unit.

24. A composition of matter in accordance with claim 23 wherein said second nuclide is selected from the same group of nuclides as said first nuclide.

25. A composition of matter in accordance with claim 22 wherein
said second nuclide is incapable of generating detectable radioactive radiation when suitable activating radiation is directed thereat, and
said first nuclide is incapable of being rendered explosively radioactive by the activating radiation for said second nuclide to permit a concentration of said drug units targeted within a living being to be first detected and located before rendering said first nuclide of such drug units destructively radioactive.

26. A composition of matter in accordance with claim 21 wherein at least one of said nuclides is selected from the group of isotopes of hydrogen, lithium, berylium, cadmium, lanthanum, actinides series of elements and transition elements.

27. A composition of mtter in accordance with claim 21 wherein at least one of said nuclides is operable to emit radiation when activated in one or more forms of atomic radiation of the group including alpha particles, beta particles, protons, gamma rays, positrons, antiprotons and the like.

28. A method of treating a malady existing in a living being, said method comprising:
(a) forming a plurality of drug units, each containing an antibody which is targeted to a specific antigen associated with such malady wherein each of said drug units also contains a normally inactive nuclide capable of being rendered radioactive with externally generated radiation applied thereto from a source of said radiation,
(b) administering said drug units to a living being whose body contains said specific antigen and allowing a quantity of said drug units to target to antigenic material at a site in the body of said living being when the antibodies of said drug units attach to respective antigens at said site,
(c) monitoring said site with radiation modulated with image information derived from said site and generating an image of said site on a viewing screen of a monitor means and determining the density, distribution and the location of the tissue of said living being containing said drug units at said site,
(d) employing the information derived from such monitoring to control the generation of and to direct a beam of activating radiation from a source external of said body of said living being through said body to intersect said units of said drug and to render said nuclide of said units radioactive at said site to radioactively treat body tissue in the immediate vicinity of said drug units.

29. A method in accordance with claim 28 wherein said malady is defined by a tumor at said site and wherein the radioactivity generated by the nuclide material rendered radioactive by said beam of radiation directed at said site is operable to destroy said tumor.

30. A method in accordance with claim 29 wherein the radiation employed to monitor said site is generated by the radioactivity of said nuclide material generated when said beam of activating radiation intersects said nuclide at said site.

31. A composition of matter in accordance with claim 21 wherein said second nuclide is capable of being rendered radioactive by externally generated radiation of an intensity which is incapable of rendering said first nuclide radioactive so as to permit radioactivity from said second nuclide to be generated for detection purposes without generating said cell destroying radiation by the activation of said nuclide.

32. The composition of matter in accordance with claim 21 wherein said first and second nuclides are selected from the group of nuclides which include boron-10, cadmium-113, lithium-6, samarium-149, mercury-199, gadolinium-155 and gadolinium-157.

33. A composition of matter in accordance with claim 21 wherein said second nuclide is provided in a substantially smaller amount than said first nuclide in said drug units.

34. A composition of matter in accordance with claim 1 wherein said first normally inactive nuclide is operable, when activated, to generate radioactivity selected from the forms of radioactivity including alpha particles, beta particles, protons, positrons, gamma rays, antiprotons and the like.

35. A method in accordance with claim 28 including
further monitoring the effects of the radioactivity generated when said beam of radiation activates said normally inactive nuclide, and
causing additional of said drug units to become targeted to said site,
thereafter directing said beam or activating radiation again at said site to render the nuclide of said additional drug units radioactive to effect further treatment of body tissue at said site.

36. A method in accordance with claim 35 wherein
said site includes cancer cells which contain the antigen to which the antibodies of said drug units are targeted, and
the steps of the method are repeated as many times as necessary to effect remission or destruction of the tumor.

37. A method in accordance with claim 28 including
further monitoring the effects of the radiation generated by said nuclide when said nuclide is activated by said beam of activating radiation to determine if further treatment is necessary, and
effecting such further treatment if necessary to cure the malady being treated.

38. A method in accordance with claim 37 including
administering an additional quantity of said drug units to the body of said living being,
repeating the monitoring step after allowing said additional units to target to antigenic material at said site to determine the density and distribution of said drug units at said site, and thereafter
again directing said beam of activating radiation at said site for a select time interval to render the nuclide of said additional units radioactive at said site to continue the treatment of body tissue.

39. A method in accordance with claim 38 wherein said site includes a malignancy defined by one or more cancerous tumors.

40. A method in accordance with claim 28 wherein
said monitoring is effected by including a radioactive isotope with at least a portion of said drug units targeted to antigenic material at said site in the body of said living being, and
detecting the radioactivity of said isotope at said site to generate said image.

41. A method in accordance with claim 40 wherein
said antigenic material is associated with the cells of a tumor at said site, and
the image generated defines the shape and location of said tumor.

* * * * *